(12) United States Patent
Wiesauer et al.

(10) Patent No.: US 6,482,159 B1
(45) Date of Patent: Nov. 19, 2002

(54) METHOD FOR THE EXAMINATION OF OBJECTS WITH ULTRASOUND

(75) Inventors: Franz Wiesauer, Zipf; Arthur Gritzky, Pollham, both of (AT); Min Hwa Lee, Seoul (KR)

(73) Assignee: GE Medical Systems Kretztechnik GmbH & Co oHG, Zipf (AT)

( * ) Notice: Subject to any disclaimer, the term of this patent is extended or adjusted under 35 U.S.C. 154(b) by 0 days.

(21) Appl. No.: 09/515,531

(22) Filed: Feb. 29, 2000

(30) Foreign Application Priority Data

Mar. 9, 1999 (EP) .............................. 99890078

(51) Int. Cl.[7] .............................................. A61B 8/00
(52) U.S. Cl. ...................................... 600/443; 128/916
(58) Field of Search ................................. 600/437, 443, 600/445, 447, 454, 458; 367/138; 73/607, 620, 625, 626; 128/916

(56) References Cited

U.S. PATENT DOCUMENTS

| | | | |
|---|---|---|---|
| 4,271,706 A | * | 6/1981 | Ledley ........................ 128/916 |
| 5,485,842 A | | 1/1996 | Quistgaard |
| 5,645,066 A | | 7/1997 | Gandini et al. |
| 5,779,641 A | | 7/1998 | Hatfield et al. |
| 5,797,844 A | | 8/1998 | Yoshioka et al. |
| 5,871,019 A | | 2/1999 | Belohlavek |

FOREIGN PATENT DOCUMENTS

| | | |
|---|---|---|
| AU | 358 155 | 8/1980 |
| AU | 001 708 U2 | 10/1997 |

OTHER PUBLICATIONS

Sussner et al, "Contour Detection Using Artificial Neuronal Network Pre-segmentation", Computers in Cardiology 1995, Vienna, Austria, Sep. 1995, pp. 737–740.

Strohmer et al, "How To Recover Smooth Object Boundaries in Noisy Medical Images", Proceedings of the International Conference on Image Processing, IC Lausanne, Sep. 1996, pp. 331–334—Institute of Electrical and Electronics Engineers.

* cited by examiner

*Primary Examiner*—Marvin M. Lateef
*Assistant Examiner*—Ali Imam
(74) *Attorney, Agent, or Firm*—Collard & Roe, P.C.

(57) ABSTRACT

For that method to examine an object by using ultrasound waves a spatial region of the object is scanned by a 3D probe. From the reflected echo signals just signals are processed which fulfil certain selectable criteria and taken to display it according to their position on at least one display device. For the representation of one or more objects with one or more interesting layers the geometrical selection criterion is a shell which approximates a surface of the object or of a layer and which can have a certain thickness, and only signals which are selected by this shell will be processed and displayed. This results in a undisturbed representation of the object and allows better view to the characteristic of the surface regarding structure or perfusion.

11 Claims, 2 Drawing Sheets

METHOD FOR THE EXAMINATION OF OBJECTS WITH ULTRASOUND

BACKGROUND OF THE INVENTION

1. Field of the Invention

The present invention relates to a method for the examination of objects with ultrasound for which a spatial region of the object is scanned by using a 3D ultrasound probe and for which from the reflected echo-signals only those signals are selected which fulfill selectable requirements and are used to generate an image on at least one display according to the spatial position in which the echo is reflected.

2. Description of the Prior Art

Scanning a spatial region of an object and storing the echo information on an address which corresponds to the geometrically correct position is known (AT 358 155 B). For this purpose, a scan plane (B-mode or C-mode) is moved over the object which has to be examined. This scan is done either manually (together with a simultaneous detection of the position of the plane to a reference position) or by using a specialized 3D probe which does the movement of the scan-plane in an automated way (e.g. AT 1708 GM). This volume-scan is done by acquiring a cross-sectional plane which is scanned either by using a mechanically moved transducer or by using an electronic multielement probe whereby this cross-sectional plane is moved simultaneously in a direction more or less orthogonal to the cross-sectional plane. This method allows to reconstruct the echo-information in planes which are arbitrarily positioned inside the scanned volume and which are no longer related to the cross-sectional planes used during data acquisition. That means it allows to produce images which cannot be achieved by standard ultrasound scanning due to anatomical reasons. Different visualization algorithms are able to reconstruct echoes from a reflecting surface in a way that the observer has a 3D impression of the object. The viewing angle from which the object is reconstructed is independent from the direction of the ultrasound beams which were used for the data acquisition. Therefore, the observer can "walk" virtually around the object and observe the images from the reconstructed object from different viewing angles on a display. Even for this standard method, a critical issue is the removal of unwanted echoes in front of the object which interfere with the reconstruction of the object of interest. We can find a typical scenario in obstetric applications when the fetus should be examined by abdominal scanning. In that case, there is maternal tissue between the probe and the fetus which covers the face and body of the fetus. Up to now, a simply shaped region of interest (e.g. cube) is selected which contains mainly the object but still some interfering or unwanted information. This described method contains no further information concerning the actual surface of the object and needs also some skills to select the region of interest in a proper way. Additionally, the characteristic of the surface can be important for the examination of the object of interest, such as the perfusion of a tissue on the surface of a tumor or the structure of the vessel which penetrate the tumor.

SUMMARY OF INVENTION

The present invention improves the method described above with the aim to significantly simplify the user interaction necessary for the representation of an object or the representation of a certain layer within the volume of interest and furthermore to allow to characterize the surface of an object of interest (e.g. perfusion).

This aim is accomplished in that, based on the method described above, a shell is determined which corresponds to a surface or a layer of the object of interest, and only echo information inside this geometrically defined region is used for further processing.

The detection of the surface can be done in an automated way when the echoes coming from this surface are well defined. But also a semi-automated method is possible that means that the contour is edited manually to correct the contours so that it matches the surface in the best way. Finally, the surface is defined by the points of the surface, which are found in the contouring process, by a "wire-model" which connects the points and an interpolation procedure which defines all parts of the surface in between. This defines the object "shell" of the present invention. It is possible to eliminate for the processing all echoes which are outside the shell, so the result is a clear view to the object of interest. The main intention of the present invention is to characterize the surface of an object beside the standard 3D representation of the object.

According to a further feature of the present invention, the thickness of the shell can be varied between approximately "zero" and a thickness which comprises the complete size of the object. In this way, information coming only from the surface or further information from the object can be processed, which can be displayed for example in reconstructed cross-sectional planes containing only data which are defined by the shell. The selection of shells with different thickness or the continuous variation of the thickness results in additional information—e.g. if Doppler signals are processed—regarding the perfusion or the structure of the blood flow. Another possibility is that a certain thickness is chosen and—for convex objects by diminishing the diameter of the shell—the object is examined layer by layer.

According to another feature of the present invention, a histogram is calculated from the selected information—data which correspond either to amplitude or to flow information or to other parameters which can be derived from the ultrasound signal.

The resulting images can be displayed individually. A good choice e.g. is for the first overview a transparent 3D representation. Another option of the present invention is also to display simultaneously a variety of images as e.g. a 3D image combined with a histogram of the flow distribution on the surface of the object whereby the surface is superimposed to the 3D image so that the complex spatial relationship can be visualized.

To document a result or to give an overview, the information in a shell can also be projected/unwound into a plane display by using algorithms which are used for maps.

Further details and advantages of the present invention can be found in the drawings which are described below. The drawings describe a preferred embodiment of the present invention.

DETAILED DESCRIPTION OF THE PREFERRED EMBODIMENT

Figure 1:
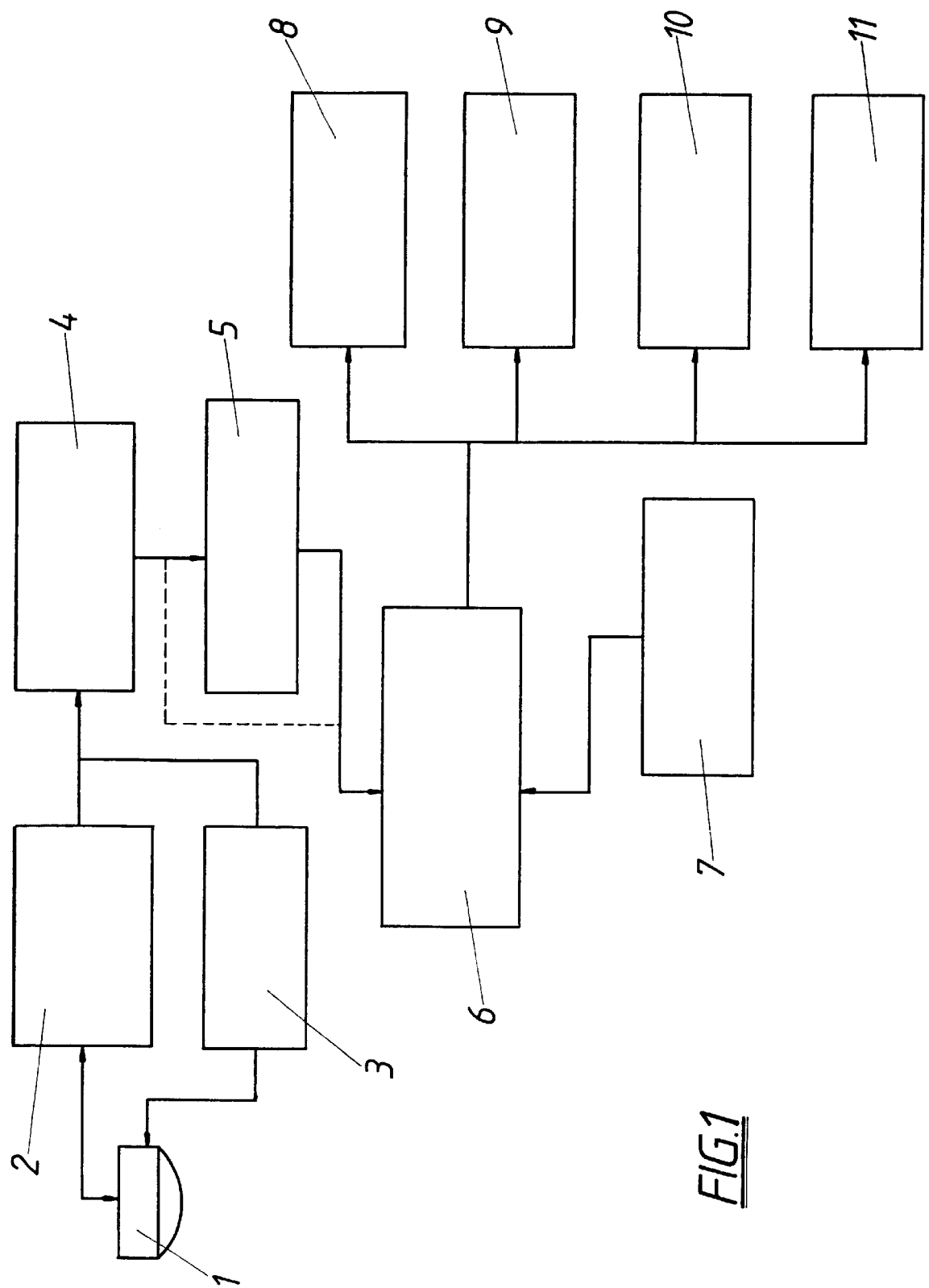
FIG. 1 is a diagram showing the elements of an ultrasound unit in one embodiment of the present invention.

According to FIG. 1, a 3D probe scans a larger spatial area in an object. The ultrasound echo-processor 2 transmits the ultrasound pulses and receives the reflected echoes. The 3D movement is determined by the control unit 3 which controls the position of the transducer 1 as well as the precise time to transmit an ultrasound pulse. Furthermore, it controls also the storage device 4 in which the reflected echo-signals are stored according to the position of the reflector. If needed, an echo-interpolator 5 can be provided. From the storage device 4 the echo-data are transferred to the storage device 6 for storing Cartesian coordinates, i.e. a certain increment/decrement in address corresponds to a certain increment/decrement in orthogonal spatial distances. From this storage device 6, the signals are accessed from an access unit 7, the processing of the data being done in different units 8, 9, 10, 11. The processing unit 8 reconstructs several cross sectional planes which are arbitrarily positioned within the scanned volume, the processing unit 9 performs a volume rendering process resulting in images which give a 3D impression to the observer, the processing unit 10 calculates a wire model of the surface of interest and finally, processing unit 11 processes the dataset—using results from unit 10 using the object "shell" according to the present invention.

Figure 3:
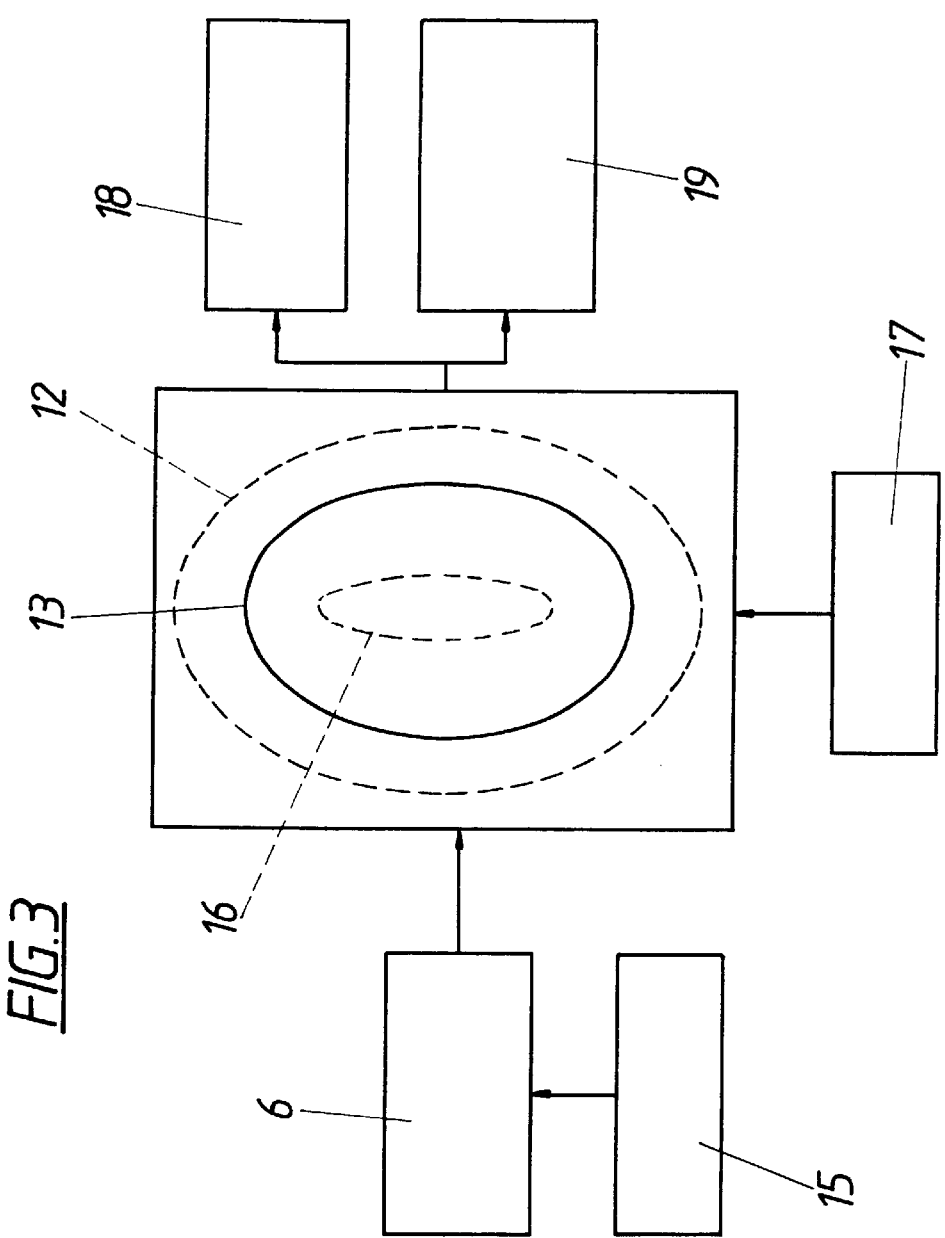
FIG. 3 shows schematically the elements including software modules which are needed to make this selection.
Figure 2:
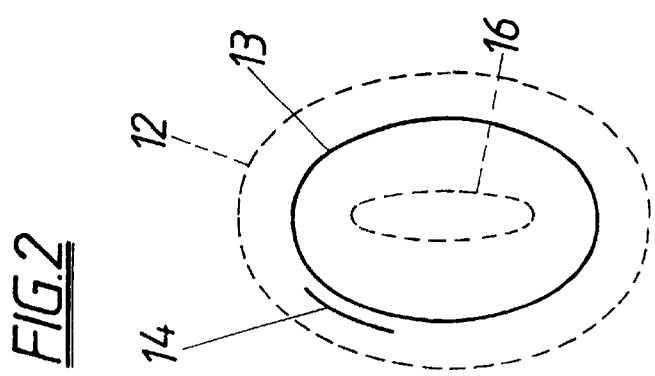
FIG. 2 is a schematic cross-sectional area to show the selection steps for the present invention.

As already mentioned in the general description of the present invention, a surface of a scanned object or a certain layer of the object should be selected, processed and displayed. In FIG. 2, a dotted line 12 shows the contour of the total volume which has been scanned. Inside this scanned volume is an object of interest of which the surface 13 is shown in the drawing. To achieve this, different methods are possible. For an automated detection, different cross sectional planes are taken to determine the echoes which are reflected from the surface 13. If this is done in several planes covering the total object of interest, the surface is represented as a wire model which can be supplemented by interpolation procedures to describe the complete surface of the object, similarly to the way it is done in CAD software. It is also possible to show a contour line 14 in reference to the scanned volume 12 which can be manipulated until a sufficient coincidence is achieved with the surface 13 of the object so that then a "shell" is defined. This approximation process can also be done automated. If the surface of an object is now determined, the addresses corresponding to the surface are stored in the control unit 5 (see FIG. 3). It should be mentioned that the shell which defines the data area to be evaluated can be the surface 13 itself, or an area defined by the surface and by a selectable thickness which can expand from the surface to the inside of the object, to the outside of the object or in both directions. FIG. 2 shows a shell 16 which is expanded to the inside of the object.

For the further processing, only data which correspond with the surface 13 or with a shell around this surface as described above will be transferred from storage device 6 by control unit 15. The processing itself (gray-values, flow-information etc.) is determined by the processor 17. Software module 18 the complete surface of the object of interest and via module 19 the size of the shell.

The different methods for the data representation were described in the general description. The complete system and parts for 3D representation have been disclosed in our EP 98 890 169.0 of Jun. 4, 1998.

What is claimed is:

1. A method of examining an object with ultrasonic waves, comprising the steps of
   (a) scanning a spatial region of the object containing a selected spatial region with a 3D ultrasound probe transmitting the ultrasonic waves and receiving echo signals from the scanned spatial region,
   (b) evaluating the echo signals from the scanned spatial region on the basis of selection criteria limited at least approximately to the echo signals received from the selected spatial region,
      (1) unambiguously associated cross-sectional planes passing through the spatial region and containing the selected spatial region providing the selection criteria,
   (c) searching for those echo signals in the cross-sectional planes determining the boundary of the selected spatial region,
      (1) those echo signals establishing a scanning pattern defining a shell around a surface of the selected spatial region, and
   (d) using only those echo signals defining the shell for creating an image on at least one display device.

2. The method of claim 1, wherein the shell varies between a thickness of approximately zero and to a thickness corresponding to that of the cross-sectional planes.

3. The method of claim 1, wherein those echo signals are subjected to a histogram evaluation and are used to create a corresponding image.

4. The method of claim 3, wherein the corresponding image is superimposed upon a 3-D image of the object.

5. The method of claim 1, wherein those echo signals are subjected to a Doppler evaluation and are used to create a corresponding color image.

6. The method of claim 5, wherein the color image is superimposed upon a 3D image of the object.

7. The method of claim 1, wherein the shell is developed onto a plane for creating the image.

8. The method of claim 1, wherein the selected spatial region is a surface of a human body.

9. The method of claim 1, wherein the selected spatial region is an intermediate layer of a human body.

10. The method of claim 1, wherein those echo signals are searched on the basis of the intensity of their reflection properties.

11. The method of claim 1, wherein those echo signals are searched by manual adjustment in the image of the cross-sectional plane.

* * * * *